(12) United States Patent　(10) Patent No.: US 8,106,781 B2
Pietersen　(45) Date of Patent: Jan. 31, 2012

(54) DEVICE FOR MONITORING THE CONDITION OF A HUMAN BEING

(76) Inventor: Johannes De Klerk Pietersen, Stellenbosch (ZA)

( * ) Notice: Subject to any disclaimer, the term of this patent is extended or adjusted under 35 U.S.C. 154(b) by 0 days.

(21) Appl. No.: 12/856,476

(22) Filed: Aug. 13, 2010

(65) Prior Publication Data

US 2011/0034820 A1　Feb. 10, 2011

Related U.S. Application Data

(63) Continuation of application No. 11/307,361, filed on Feb. 2, 2006, now Pat. No. 7,800,505.

(51) Int. Cl.
*G08B 23/00* (2006.01)

(52) U.S. Cl. ............... 340/573.1; 340/517; 340/604

(58) Field of Classification Search ............ 340/573.1, 340/517, 539.12, 575, 573.7, 626, 665, 604, 340/407.1; 600/301, 529, 533, 534
See application file for complete search history.

(56) References Cited

U.S. PATENT DOCUMENTS

| | | | |
|---|---|---|---|
| 4,205,672 A | 6/1980 | Dvorak | |
| 5,247,944 A * | 9/1993 | Hirano et al. | 600/595 |
| 5,277,194 A | 1/1994 | Hosterman | |
| 5,568,128 A | 10/1996 | Nair | |
| 5,709,222 A | 1/1998 | Davallou | |
| 5,749,365 A | 5/1998 | Magill | |
| 5,808,540 A * | 9/1998 | Wheeler et al. | 338/114 |
| 5,928,157 A | 7/1999 | O'Dwyer | |
| 5,993,397 A * | 11/1999 | Branson | 600/534 |
| 6,097,297 A | 8/2000 | Fard | |
| 6,267,730 B1 * | 7/2001 | Pacunas | 600/534 |
| 6,450,168 B1 | 9/2002 | Nguyen | |
| 6,573,837 B2 | 6/2003 | Bluteau | |
| 2002/0008630 A1 | 1/2002 | Lehrman et al. | |
| 2002/0013538 A1 | 1/2002 | Teller | |
| 2002/0124295 A1 | 9/2002 | Fenwick et al. | |
| 2003/0126593 A1 | 7/2003 | Mault | |
| 2006/0097879 A1 * | 5/2006 | Lippincott | 340/573.1 |

FOREIGN PATENT DOCUMENTS

DE　42 14 263 A　11/1993
DE　100 05 526 A　8/2001

* cited by examiner

*Primary Examiner* — Toan N Pham
(74) *Attorney, Agent, or Firm* — Hahn Moodley LLP; Vani Moodley, Esq.

(57) ABSTRACT

A device for continuously monitoring one or more indicators relating to the health or comfort of a person 12 includes one or more sensing means for measuring a value of one or more desired indicators and a communicating means 13 communicating an alarm signal when the measured value is above or below a predetermined value or range of values range, wherein the device 10 is adapted to be attached to an item of clothing 14 of the person 12.

18 Claims, 6 Drawing Sheets

DEVICE FOR MONITORING THE CONDITION OF A HUMAN BEING

CROSS-REFERENCE TO RELATED APPLICATIONS

This application is an U.S. national phase application under 35 U.S.C. §371 based upon co-pending International Application No. PCT/ZA2004/00009 filed Aug. 4, 2004. Additionally, this U.S. national phase application claims the benefit of priority of co-pending International Application No. PCT/ZA2004/00009 filed Aug. 4, 2004, South African Application No. ZA 2003/0949 filed Aug. 4, 2003, South African Application No. ZA 2003/6138 filed Aug. 8, 2003, and South African Application No. ZA 2003/8285 filed Oct. 24, 2003. The entire disclosures of the prior applications are incorporated herein by reference. The international application was published in the English language on Feb. 10, 2005 under Publication No. WO 2005/011491.

FIELD OF THE INVENTION

This invention relates to a device for monitoring one or more indicators relating to the health or comfort of a human being and for communicating the sensed information to a caretaker of the human being.

BACKGROUND TO THE INVENTION

Monitors for sensing the heart rate, breathing or other vital functions of a hospitalized person are well known in the art. Devices for home use have been developed to aid in the care of infants or elderly persons to monitor breathing, heart rate, and the like. These devices are however often too complicated to be operated by an unskilled person and/or cause discomfort to the person being monitored.

In U.S. Pat. No. 5,400,012, a breathing monitor is disclosed for detecting Sudden Infant Death Syndrome (SIDS) in infants caused by apnea, which monitor includes an enclosure that is attached to the torso of an infant using a strap. The enclosure is supported by and isolated from the infant's torso by a fluid filled bladder coupler such that there is no direct contact between the enclosure and the torso of the infant. A monitor including a piezoelectric element is connected to the fluid coupler and a battery powered electronic circuit contained in the enclosure flashes an LED as the infant breathes and sounds and alarm should the infant fail to exhale for a predetermined period of time. An adjustable strap connector for the strap provides visual indication of the strap being correctly attached and a limited range of motion is permissible between the strap and the enclosure when the infant breathes.

In U.S. Pat. No. 4,146,885 a hospital bed or mattress for infants including a respiration monitor and alarm to detect apnea is disclosed. The infant's breathing causes slight displacements of portions of its body which in turn transmit dynamic recoil forces to the bed on which the infant is resting.

The monitors disclosed in the prior art suffer from a number of drawbacks. A most basic disadvantage of known monitors is that securing the device to the body of an infant is a cumbersome task which does not encourage use of the device. Known devices are in addition uncomfortable to wear, easily become displaced in use and require a skilled user.

The inventor therefore believes that a need exists for a device for monitoring various indicators relating to the health or comfort of an infant or grown person and for communicating information to a caretaker of the infant or grown person and which device overcomes at least some of the disadvantages of the prior art.

SUMMARY OF THE INVENTION

According to the invention, there is provided a device for continuously monitoring one or more indicators relating to the health or comfort of a person, the device including:
one or more sensing means for sensing and measuring a value of one or more desired indicators; and
a communicating means for communicating an alarm signal when the measured value is above or below a predetermined value or range of values, wherein the device is adapted to be attached to an item of clothing of the person.

The desired indicator may be selected from the group including: breathing, heartbeat, temperature, and humidity.

The sensing means may be located in a housing of the device.

The device may include a clip extending from the housing so that it is attachable to the waistband of an item of clothing worn by the person being monitored. In the case of an infant, the device may be attached to a waistband of a diaper worn by the infant. In the case of an adult, the device may be attached to a waistband of an undergarment worn by the adult.

The sensing means for sensing and measuring breathing of the person may be in the form of a pressure transducer which in use is located between the item of clothing and the skin of the person wearing the device. The pressure transducer may measure pressure exerted on it by the lifting and falling of the skin of the breathing person. When the pressure exerted on the pressure transducer occurs in irregular intervals or ceases for a predetermined period of time, this may activate the communicating means.

When the pressure transducer measures pressure that occurs in irregular intervals or ceases for a predetermined period of time, it may activate a stimulating means aimed at encouraging the person to breathe normally either prior to or simultaneously with activating the communicating means. The stimulating means may be in the form of a conventional vibrating mechanism that causes the housing of the device to vibrate.

The sensing means for sensing and measuring the breathing of a person may be sufficiently sensitive to additionally sense the heartbeat of a person. When an irregular heartbeat or a cessation in heartbeat is sensed, this may activate the communicating means.

The device may include a further sensing means for sensing temperature and which in use is located between the item of clothing and the skin of the person wearing the device. The temperature sensor may continuously sense and measure temperature and may activate the communicating means should the measured temperature be below or above a predetermined value or value range.

Additionally, a sensing means for sensing temperature and which is in use located exterior the item of clothing of the person wearing the device, may be provided. The values measured by the two temperature sensors may be compared continuously so as to calculate the rate of heat loss of the person wearing the device. When the rate of heat loss falls below or rises above a predetermined value or range of values, this may activate the communicating means.

The device may include yet a further sensing means for sensing and measuring humidity and that is in use located between the item of clothing and the skin of the person wearing the device. When the value of the humidity rises above a certain predetermined value, this may activate the communicating means.

Additionally, a sensing means for sensing humidity and which is in use located exterior the item of clothing of the person wearing the device, may be provided. The values measured by the two humidity sensors may be compared continuously so as to be able to ascertain when the humidity level between the item of clothing and skin of the person rises above a desired value at which stage the communicating means may be activated.

The humidity sensor may be in the form of a conductivity sensor. As an increase in humidity leads to an increase in conductivity, when the conductivity rises above a predetermined value, the communicating means may be activated.

The sensing and measuring of humidity is particularly useful when the device is used to monitor an infant, in that an increase in humidity indicates a soiled diaper which can then be changed timeously by a caretaker of the infant before any discomfort is caused.

The communicating means may include one or more of the following: an audible alarm, a visual signal such as a flashing light, and a radio signal transmitted to a suitable remotely located receiver.

The housing and clip may be manufactured from any suitable synthetic plastics material.

The device may include a power source in the form of, for example, batteries located in the housing.

The device may include an interface on the housing to permit setting of the various values or value ranges at which the communicating means is to be activated and for switching the device on and off. The housing may be provided with a cover for covering the interface so as to inhibit the device from accidentally being turned off or reprogrammed during use.

The device may be provided with a data storage device for storing the information sensed by the sensing means. A user may retrieve the stored data at any time for the purpose of analysis.

The invention extends to an item of clothing which includes a device as described above.

DETAILED DESCRIPTION OF THE INVENTION

The invention will now be described by way of the following non-limiting examples with reference to the accompanying drawings.

Figure 1:
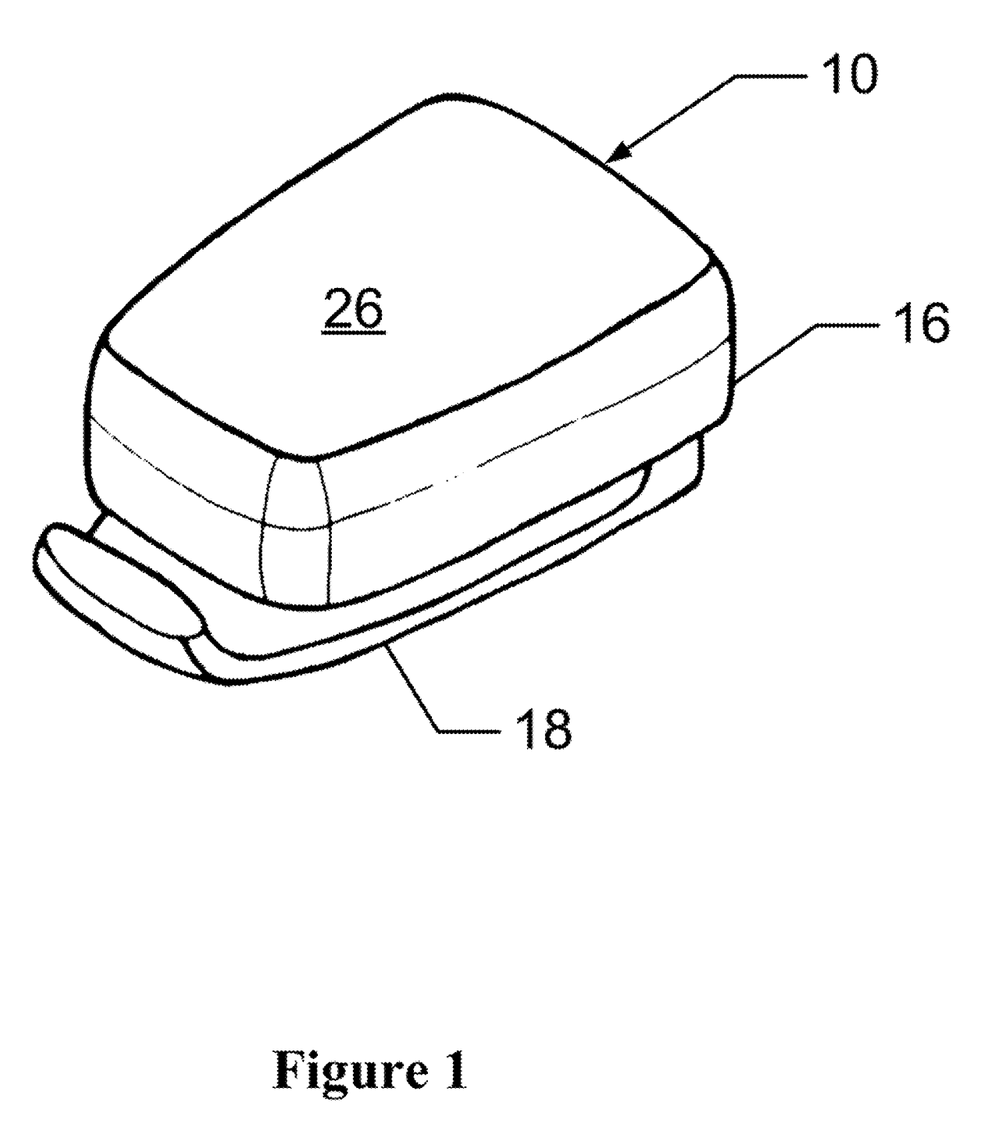
FIG. 1 shows a first isometric view of a device in accordance with the present invention.
Figure 2:
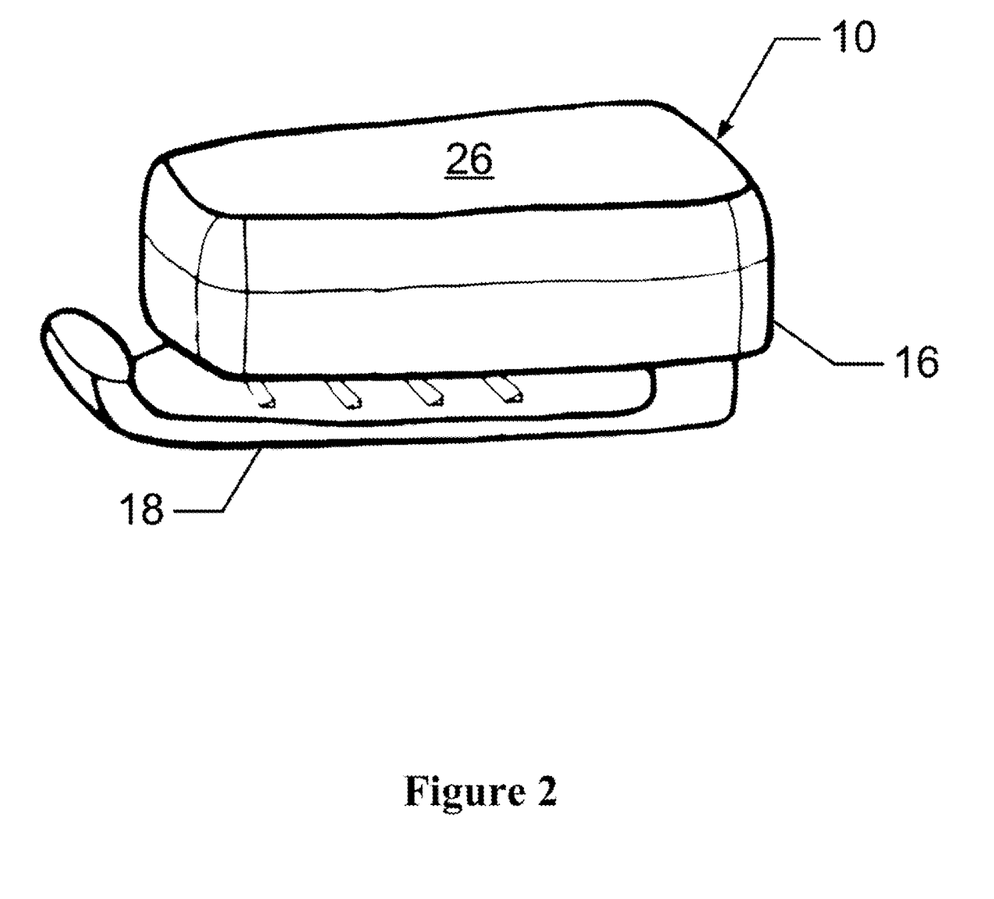
FIG. 2 shows a second isometric view of the device of FIG. 1.
Figure 3:
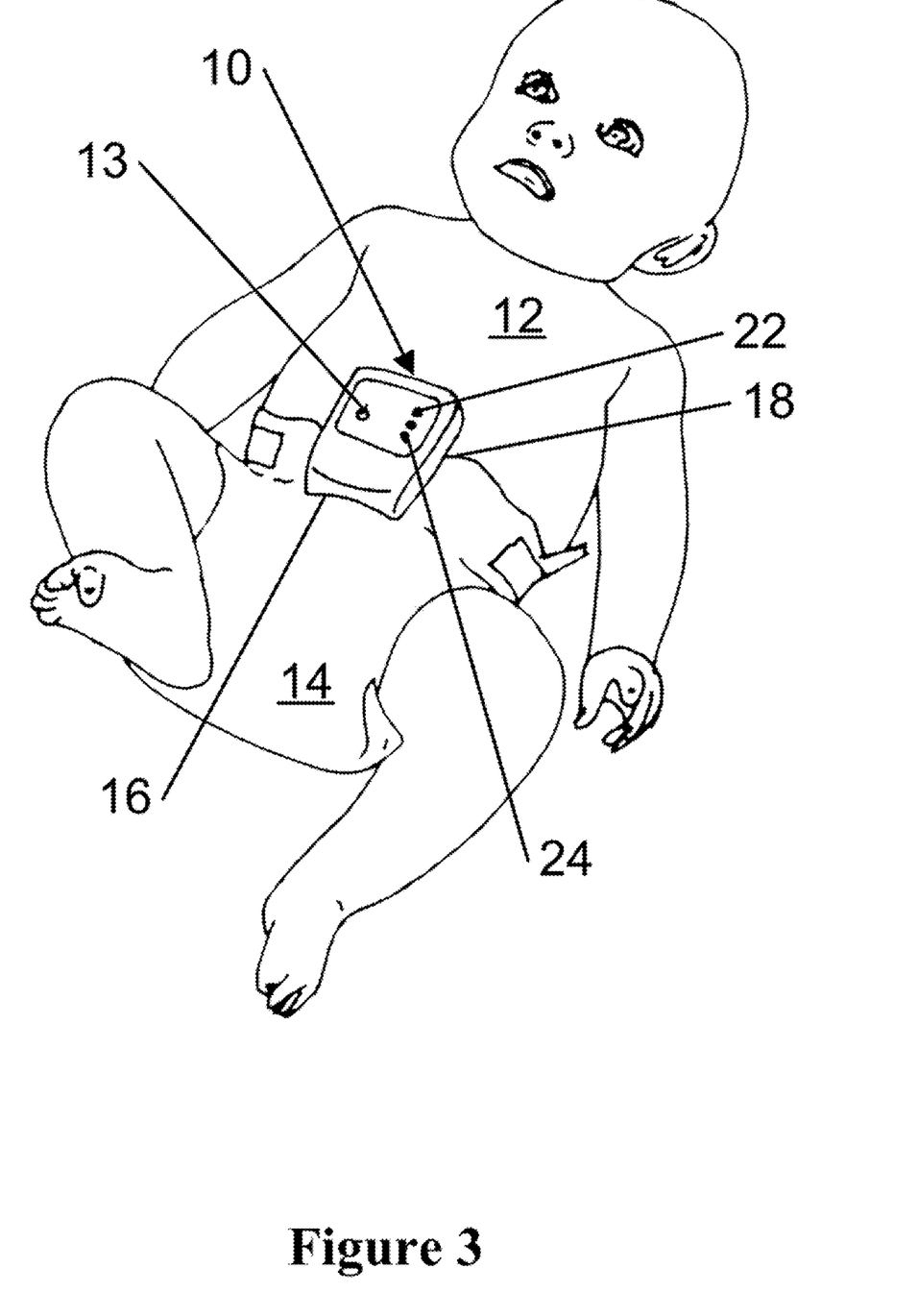
FIG. 3 shows an isometric view of the device of FIG. 1 in use when attached to the diaper of an infant.
Figure 4:
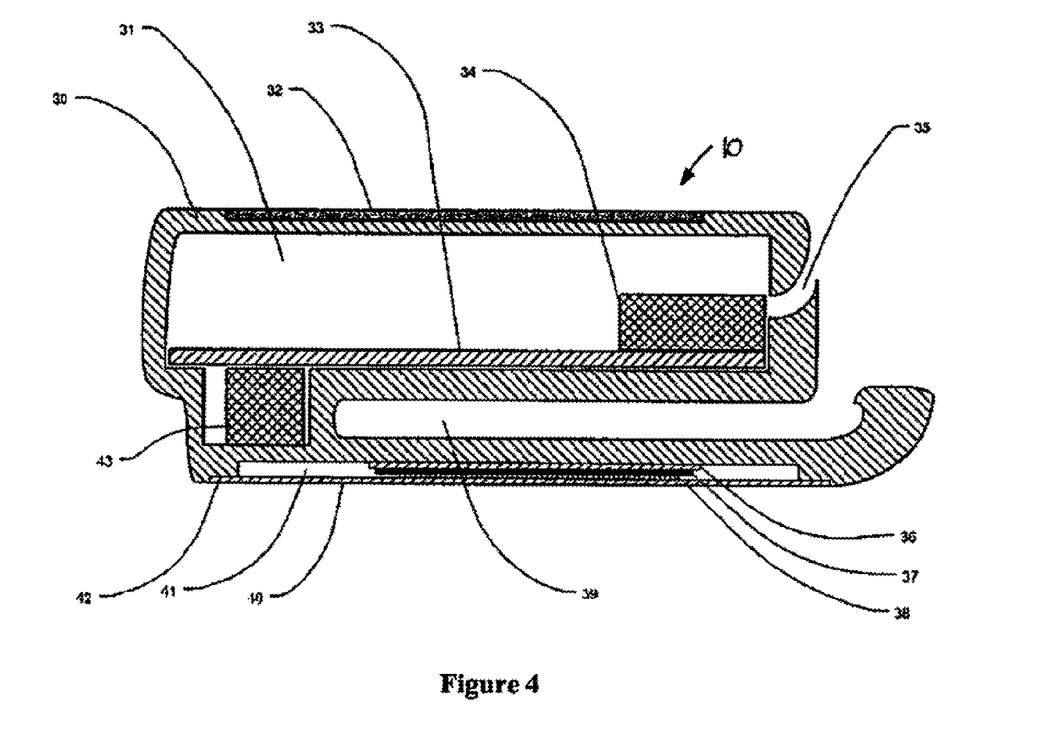
FIG. 4 shows a cross sectional side view an alternative embodiment of a device in accordance with the present invention.
Figure 5:
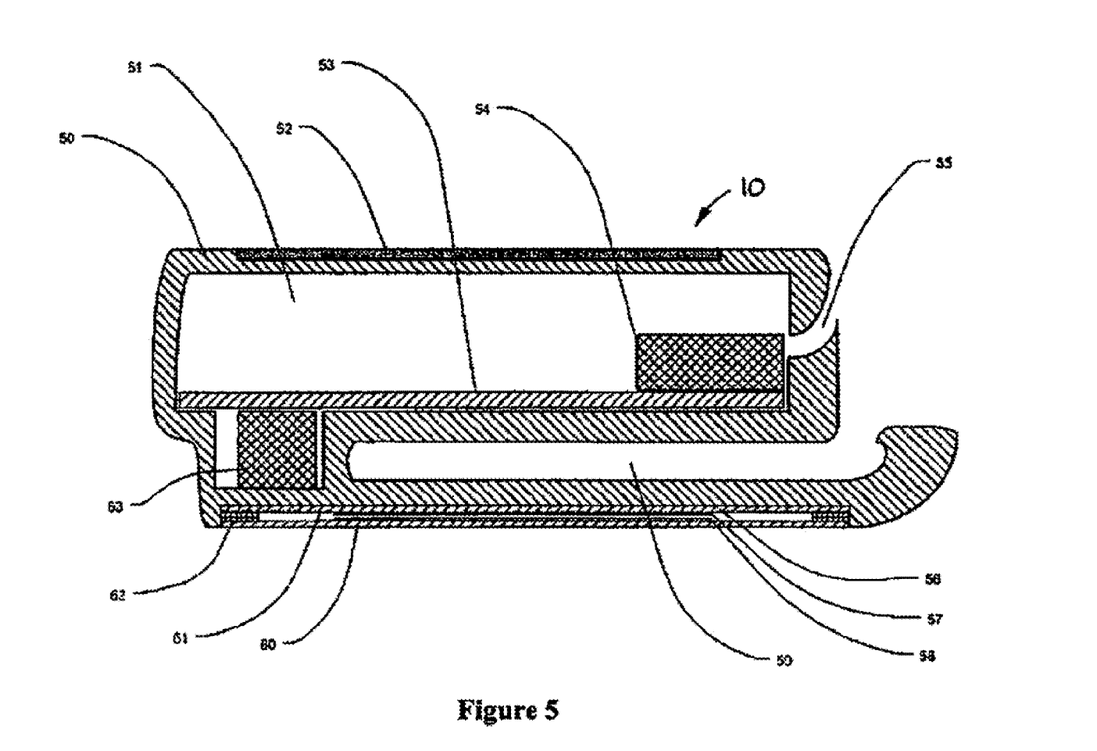
FIG. 5 shows a cross sectional side view an alternative embodiment of a device in accordance with the present invention.
Figure 6:
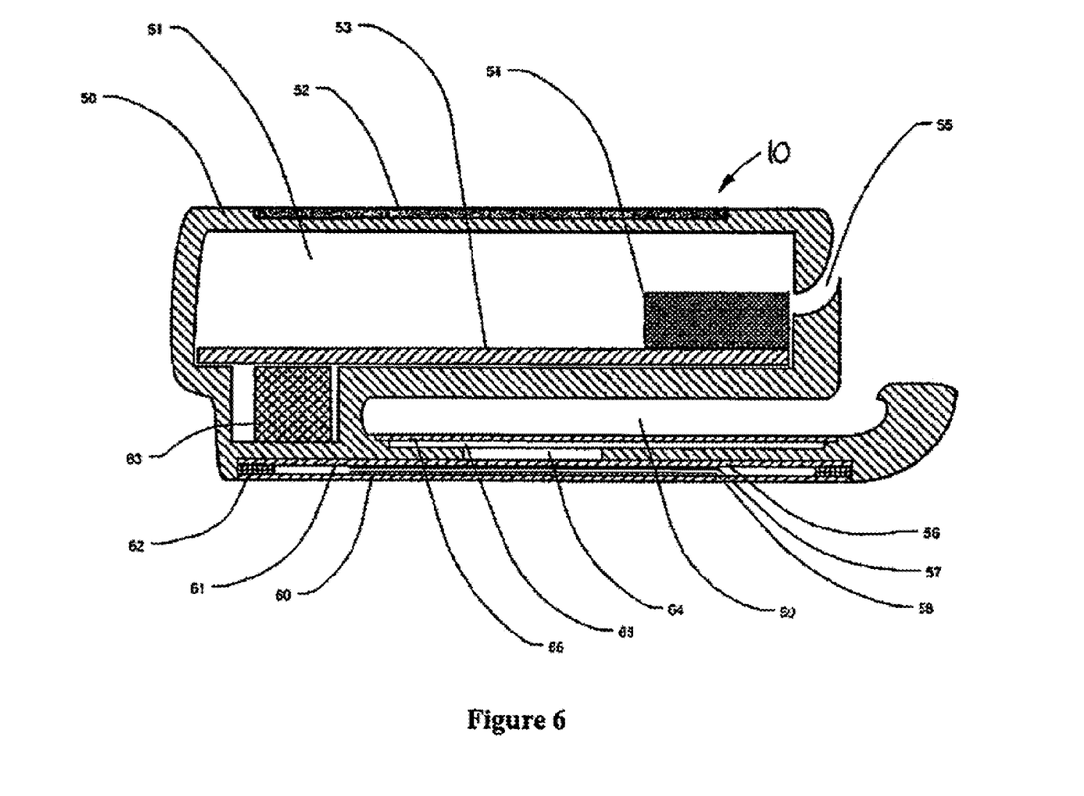
FIG. 6 shows a cross sectional side view an alternative embodiment of a device in accordance with the present invention.

In the drawings: —FIG. 1 shows a first isometric view of a device in accordance with the present invention; FIG. 2 shows a second isometric view of the device of FIG. 1; FIG. 3 shows an isometric view of the device of FIG. 1 in use when attached to the diaper of an infant; and FIGS. 4, 5, and 6 show cross sectioned side views showing details of three alternative constructions of a device in accordance with the present invention.

In the drawings, reference numeral 10 generally indicates a device for continuously monitoring one or more indicators relating to the health or comfort of a person 12 in accordance with the present invention. In the embodiment shown the person 12 is an infant.

The device 10 includes one or more sensing means for sensing and measuring a value of one or more desired indicators and a communicating means 13 communicating an alarm signal when the measured value is above or below a predetermined value or range of values, wherein the device 10 is adapted to be attached to an item of clothing 14 of the person 12.

The desired indicator includes breathing, temperature, and humidity.

The sensing means is located in a housing 16 of the device 10. The device 10 includes a clip 18 extending from the housing 16 so that it is attachable to the waistband 20 of an item of clothing 14 (in this case a diaper) worn by the person 12 being monitored.

The sensing means for sensing and measuring breathing of the person 12 is in the form of a pressure transducer which in use is located between the item of clothing 14 and the skin of the person 12 wearing the device 10. The pressure transducer measures pressure exerted on it by the lifting and falling of the skin of the breathing person 12. When the pressure exerted on the pressure transducer occurs in irregular intervals or ceases for a predetermined period of time, this activates the communicating means 13.

When the pressure transducer measures pressure that occurs in irregular intervals or ceases for a predetermined period of time, it activates a stimulating means aimed at encouraging the person 12 to breathe normally either prior to or simultaneously with activating the communicating means 13. The stimulating means is in the form of a conventional vibrating mechanism that causes the housing 16 of the device 10 to vibrate.

The device 10 includes a further sensing means for sensing temperature and which in use is located between the item of clothing 14 and the skin of the person 12 wearing the device 10.

The temperature sensor continuously senses and measure temperature and activates the communicating means 13 should the measured temperature be below or above a predetermined value or value range.

The device 10 includes yet a further sensing means for sensing and measuring humidity that is in use located between the item of clothing 14 and the skin of the person 12 wearing the device 10. When the value of the humidity rises above a certain predetermined value, this activates the communicating means 13.

The humidity sensor is in the form of a humidity sensor that measures the percentage humidity present in the air. The humidity sensor is an electronic component. When the humidity rises above a predetermined value, the communicating means 13 is activated.

The sensing and measuring of humidity is particularly useful when the device 10 is used according to the embodiment shown, in that an increase in humidity indicates a soiled diaper which can be changed timeously by a caretaker of the infant before any discomfort is caused as soon as the communication means 13 is activated.

The communicating means 13 includes an audible alarm 22 as well as a flashing light 24.

The housing 16 and clip 18 are manufactured from any suitable synthetic plastics material.

The device 10 includes a power source in the form of batteries located in the housing 16.

The device 10 includes an interface (not shown) on the housing 16 to permit setting of the various values or value ranges at which the communicating means 13 is to be activated and for switching the device 10 on and off. The housing 16 is provided with a cover 26 for covering the interface so as to inhibit the device 10 from accidentally being turned off or reprogrammed during use.

Referring now to FIG. 4:

The device 10 includes a housing 30 defining a chamber 31 for housing the electronic circuitry of the device 10. The housing 30 is manufactured from any suitable non-toxic, hypoallergenic, synthetic plastics material.

The device 10 includes a user interface panel 32 using known technology in electrical communication with the electronic circuitry. Detail of the user interface panel 32 (not shown) includes one or more push-button switches (of the type typically used in membrane keypads) for enabling and disabling the device, or for changing the settings of the device. The interface panel 32 further accommodates one or more light-emitting diodes, liquid crystal displays or other components for visual indications.

An electronic printed circuit board 33 is located in the housing 30. Various components, including a power source (typically a long-life or rechargeable battery) are affixed to the board 33. For safety reasons the housing 30 of the device 10 is permanently sealed to inhibit access to the components housed therein. However, it could also be manufactured in such a way that the user can gain access to the power source in order to replace it.

A sound transducer 34 for generating an audible alarm, such as a piezo-electric element is also included in the housing 30. An opening 35 in the housing 30 permits sound generated by the sound transducer 34 to escape from the chamber 31. Other methods of generating audible alarms and transmitting them through the housing 30 are possible and need not involve an opening.

A suitable material 36 is used to affix piezo-electric element 37 to the device 10. The element 37 can also be used as a spacer to adapt the thickness of piezo-electric element 37 to the recess depth. Alternatively, the piezo-electric element 37 can also be glued directly to the device 10.

The piezo-electric element 37 is in electrical communication with the electronic circuitry of the device 10. Applying fluctuating pressure to such an element 37 generates a corresponding fluctuating electronic potential that can be measured by the circuitry.

A suitable spacer 38 between piezo-electric element 37 and an outer membrane can be incorporated.

Slot 39 is configured and dimensioned to accommodate a the top edge of a diaper, allowing the sensor to rest against the body of an infant in order to measure changes in pressure associated with, for example, breathing. Once fitted, a typical disposable diaper's "waistband" section creates a supple but snug structure around the infant's torso. As the infant breathes its abdomen will press more and less forcefully against this waistband section of the diaper, in unison with its breathing effort. Because the device 10 is secured to this waistband section, fluctuations of the pressure exerted by the infant's abdomen will cause fluctuations of pressure against the portion of the device 10 that is located on the inside of the diaper.

An outer flexible membrane 40 is manufactured from a suitable material such as polyester or polycarbon. Pressure applied to this membrane 40 is transmitted through 38 (if present) to 37, allowing measurement of such pressure by the device 10.

Cavity 41 accommodates a sensor assembly. Cavity 41 is smaller in area than outer membrane 40, to permit an overlap 42. Outer membrane 40 is affixed to this flange by suitable means such as waterproof glue, to preventing ingress of moisture into the device 10.

Motor 43 includes and offset weight attached to spindle, commonly used for "silent ring" of cellular telephones. The offset weight causes a vibration when the motor 43 is energized, said vibration being transferred to the housing 30 of the device. This vibration is used to provide tactile stimulation to the skin of the infant under situations deemed necessary. Other means of causing tactile stimulation may be used.

Referring now to FIG. 5:

In FIG. 5, reference numerals 50 to 55, 59 and 63 represent the same elements as reference numerals 30 to 35, 39 and 43 in FIG. 4 and will therefore not be described further.

A suitable substrate 56 for a sensor is provided and is typically a membrane as used in flexible electronic circuitry, i.e. polyester or polycarbonate, suitably affixed to the device 10.

A deposit of suitable electrically resistive material 57 such as graphite paint, typically used in electronic component manufacturing, is in electrical communication with the circuitry of the device 10. A deposit 58 of suitable electrically conductive material such as conductive silver paint, typically used in electronic component manufacturing, is located on element 60. The deposit 58 is of a suitable size and shape corresponding to and aligned with that of deposit 57 over an area preferably stretching from the center of cavity 61 towards the edges of said cavity 61.

A flexible membrane 60, typically polyester, polycarbonate or similar as used in flexible electronic circuit manufacturing, and preferably hypoallergenic to prevent contact dermatitis covers deposits 57 and 58.

Pressure exerted on the membrane 60 will cause it to flex towards membrane 56. If sufficient pressure is applied, the two membranes 56 and 60 will make contact. With even more pressure, the contact area between the two membranes 56 and 60 will become larger. The electrical resistance of 57 can be measured. Forcing the two membranes 56 and 60 together will allow deposit 58 to make contact with 57. Because deposit 58 has a lower resistance than deposit 57, changing the contact area between deposits 57 and 58 will cause the measured resistance of deposit 57 to change accordingly, decreasing as more of deposit 58 makes contact with it and increasing as less of deposit 58 comes into contact with it. In practice a slight bulge (not shown) introduced below deposit 57 will cause it to remain in contact with deposit 58, allowing very slight pressures on deposit 58 to be measured.

Spacer 62 between flexible membranes 56 and 60 creates a cavity of suitable dimensions.

Spacer 62 can be coated with adhesive on both sides to allow easy assembly of the sensor as a unit, and can be made of the same materials used for membranes 57 and 60.

Referring now to FIG. 6:

A more complicated device 10 can be made by manufacturing a cavity 65 opposite the sensor, on the inside of the "clip" section. A third membrane 66 can then be affixed to that side so that it completely covers the cavity 65. A port 64 can also be made through the clip so that it connects the cavity between this membrane with the area behind membrane 57. If the port and cavity so described are then filled with fluid (and provided that portion of membrane 56 that is located underneath the graphite deposit is not permanently affixed to the housing 30 of the device 10), pressure exerted by the waistband of the diaper on membrane 66 will be transferred through the membrane by the fluid to the underside of membrane 57, pressing 57 towards 60 and allowing pressure from both sides of the clip to be measured. Such a sensor is expected to be more sensitive than those disclosed in the embodiments of FIGS. 4 and 5.

It is to be appreciated, that the invention is not limited to any specific embodiment or configuration as hereinbefore generally described or illustrated.

What is claimed is:

1. A health monitoring device for monitoring one or more parameters associated with a body of a person, the health monitoring device comprising:
    a housing; and
    a clip having a first end integral with and cantilevered to the housing and a second end remote from the first end, the clip being substantially parallel to the housing to define a slot with the housing for receiving a portion of a garment therein, whereby the health monitoring device is capable of being secured to the garment, the clip comprising a pressure sensing arrangement to convert abdominal pressure exerted on the clip due to breathing into a signal, where the housing comprises a circuit to activate an alarm based on the signal.

2. The health monitoring device of claim 1, wherein the pressure sensing arrangement comprises a piezoelectric element that generates the signal, wherein the signal is a fluctuating electronic potential corresponding to the abdominal pressure exerted on the clip, the signal is measured by the circuit, wherein the circuit activates the alarm when the signal is abnormal.

3. The health monitoring device of claim 2, wherein the pressure sensing arrangement comprises an outer flexible membrane, the outer flexible membrane is capable of transmitting the abdominal pressure exerted on the clip to piezoelectric element.

4. The health monitoring device of claim 3, wherein the outer flexible membrane is made of a polyester or polycarbon.

5. The health monitoring device of claim 1, further comprises a stimulating device coupled to the circuit and located in the housing, wherein the circuit activates the stimulating device when the signal is abnormal.

6. The health monitoring device of claim 5, the stimulating device comprises an offset weight and a motor, the motor being capable of energizing the offset weight to cause vibration when the circuit activates the stimulating device.

7. The health monitoring device of claim 1, further comprising a first temperature sensor incorporated in the clip for sensing and measuring body temperature, wherein the temperature sensor is coupled to the circuit, and wherein the circuit activates the alarm when the body temperature is abnormal.

8. The health monitoring device of claim 7, further comprising a second temperature sensor attached to the housing, the second temperature sensor measures a second temperature parameter, wherein the body temperature and the second temperature parameter are compared continuously to calculate a rate of heat loss, wherein the circuit activates the alarm when the rate of heat loss is abnormal.

9. The health monitoring device of claim 1, further comprising a first humidity sensor incorporated in the clip for sensing and measuring body humidity, wherein the humidity sensor is coupled to the circuit, and wherein the circuit activates the alarm when the body humidity is abnormal.

10. The health monitoring device of claim 9, further comprising a second humidity sensor attached to the housing member, the second humidity sensor measures a second humidity parameter, wherein the body humidity and the second humidity parameter are compared continuously to calculate a humidity level between the skin of the person and the garment, wherein the circuit activates the alarm when the humidity level is abnormal.

11. The health monitoring device of claim 1, wherein the housing comprises an opening for permitting a sound produced by the alarm to escape.

12. The health monitoring device of claim 1, wherein the housing is made of a suitable non-toxic, hypoallergenic, synthetic plastics material.

13. A health monitoring device for monitoring one or more parameters associated with a body of a person, the health monitoring device comprising:
    a housing; and
    a clip integral with the housing, wherein the health monitoring device is capable of being secured to a garment worn by the person, the clip comprising a pressure sensing arrangement to convert abdominal pressure exerted on the clip due to breathing into a signal, where the housing comprises a circuit to activate an alarm based on the signal.

14. The health monitoring device of claim 13, wherein the pressure sensing arrangement comprises a piezoelectric element that generates the signal, wherein the signal is a fluctuating electronic potential corresponding to the abdominal pressure exerted on the clip, the signal is measured by the circuit, wherein the circuit activates the alarm when the signal is abnormal.

15. The health monitoring device of claim 14, wherein the pressure sensing arrangement comprises an outer flexible membrane, the outer flexible membrane is capable of transmitting the abdominal pressure exerted on the clip to piezoelectric element.

16. The health monitoring device of claim 15, wherein the outer flexible membrane is made of a polyester or polycarbon.

17. The health monitoring device of claim 13, further comprises a stimulating device coupled to the circuit and located in the housing, wherein the circuit activates the stimulating device when the signal is abnormal.

18. The health monitoring device of claim 17, the stimulating device comprises an offset weight and a motor, the motor being capable of energizing the offset weight to cause vibration when the circuit activates the stimulating device.

* * * * *